United States Patent [19]

Tomioka et al.

[11] 4,076,931
[45] Feb. 28, 1978

[54] DERIVATIVES OF AN ANTIBIOTIC XK-62-2 AND THE PROCESS FOR THE PRODUCTION THEREOF

[75] Inventors: Shinji Tomioka, Machida; Yasuki Mori, Kawasaki, both of Japan

[73] Assignee: Abbott Laboratories, North Chicago, Ill.

[21] Appl. No.: 601,361

[22] Filed: Aug. 4, 1975

[30] Foreign Application Priority Data

Aug. 5, 1974 Japan ................................ 49-88998

[51] Int. Cl.$^2$ .............................................. C07H 15/22
[52] U.S. Cl. ...................................... 536/17; 424/180; 536/4
[58] Field of Search .................... 260/210 AB, 210 K; 536/17

[56] References Cited

U.S. PATENT DOCUMENTS

| | | | |
|---|---|---|---|
| 3,780,018 | 12/1973 | Konishi et al. | 260/210 AB |
| 3,886,139 | 5/1975 | Naito et al. | 260/210 K |

OTHER PUBLICATIONS

Okachi et al., "The Journal of Antibiotics", vol. XXVII, No. 10, 1974, pp. 793–799.
Kershner, "Kershner Thesis", 1971, pp. 101–113 pertinent, University Microfilms, High Wycomb, England.

*Primary Examiner*—Johnnie R. Brown
*Attorney, Agent, or Firm*—Fitzpatrick, Cella, Harper & Scinto

[57] ABSTRACT

New derivatives of an antibiotic XK-62-2 are produced by chemically modifying the antibiotic XK-62-2. The new derivatives are 1-N-(α-hydroxy-δ-aminovaleryl)XK-62-2 and 1-N-(α-hydroxy-ε-aminocaproyl)XK-62-2 as well as acid addition salts thereof.

5 Claims, No Drawings

DERIVATIVES OF AN ANTIBIOTIC XK-62-2 AND THE PROCESS FOR THE PRODUCTION THEREOF

DETAILED EXPLANATION OF INVENTION:

The present invention relates to derivatives of the antibiotic XK-62-2 represented by the general formula (I)

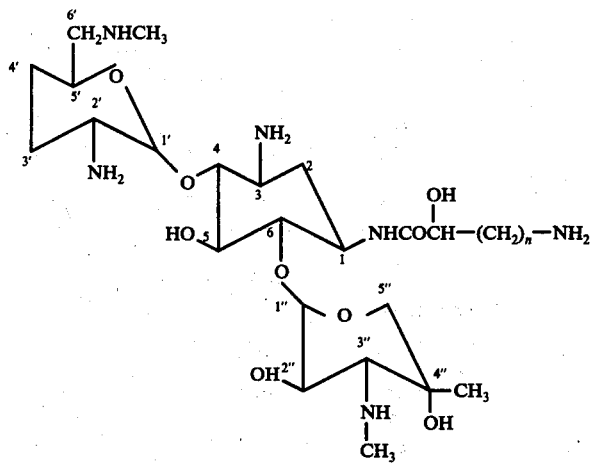

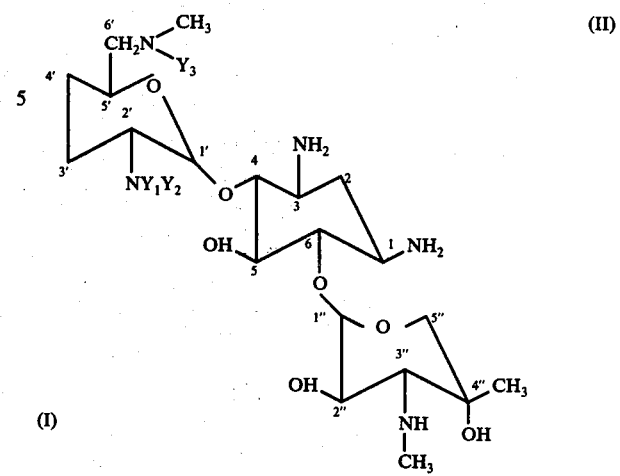

(wherein $n$ is an integer 3 or 4), their acid addition salts and the process of the production thereof. The compounds represented by the formula (I) are new compounds, which exhibit a remarkable antibacterial activity and particularly have a remarkably strong antibacterial activity against those bacteria having a resistance to the known aminoglycoside antibiotics, therefore are useful for medicine.

The acid addition salts of the compounds represented by the general formula (I) are limited to acid addition salts with the pharmaceutically acceptable non-toxic acids including various inorganic acids such as hydrochloric acid, hydrobromic acid, hydriodic acid, sulfuric acid, phosphoric acid, carbonic acid, etc., and various organic acids such as acetic acid, fumaric acid, malic acid, citric acid, mandelic acid, tartaric acid, succinic acid, ascorbic acid, etc.

The process of the present invention is that of producing new derivatives of an antibiotic XK-62-2 represented by the general formula (I), which comprises reacting an antibiotic XK-62-2 or the derivatives thereof whose amino groups bonded to the carbon atoms at the 2'- and/or 6'-positions are protected, represented by the formula (II):

[wherein $Y_1$, $Y_2$ and $Y_3$ represent hydrogen atoms or aminoprotecting groups (the formula (II) represents XK-62-2 in case of $Y_1=Y_2=Y_3=H$)] with an acylating agent such as α-hydroxy-δ-aminovaleric acid, α-hydroxy-ε-aminocaproic acid represented by the general formula (III):

(wherein one of $Y_4$ and $Y_5$ is hydrogen atom and the other one is amino-protecting group or $Y_4$ and $Y_5$ may form a ring with the nitrogen atom to which $Y_4$ and $Y_5$ are bonded and n is an integer 3 or 4) and reactive derivatives at the carboxyl groups which are functionally equivalent thereto in a suitable solvent, to prepare compounds represented by the general formula (IV):

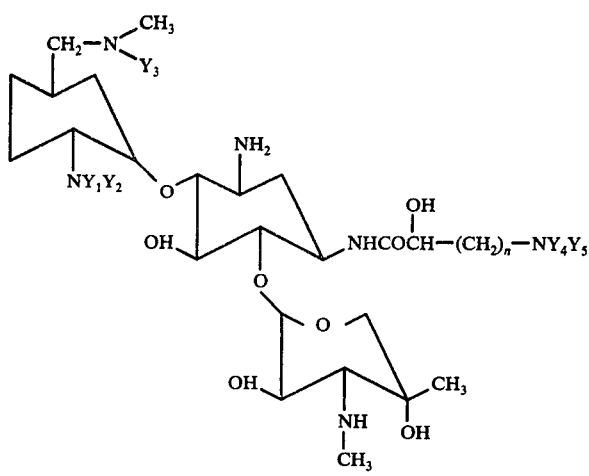

(wherein $Y_1$, $Y_2$, $Y_3$, $Y_4$, $Y_5$ and $n$ have the same significance as defined above) and eliminating the amino-protecting groups of the compounds of the formula (IV).

The starting material, an antibiotic XK-62-2 in the present invention is the known compound produced by culturing actinomycetes described and claimed in Japanese unexamined published Patent Applications Nos. 74-13391 and 74-47590 and U.S. Patent application Ser. No. 364,058, filed May 5, 1973.

The present inventors have carried out studies on the chemically modified derivatives of an antibiotic XK-62-2. They have found that compounds represented by the formula (I) have a remarkably strong antibacterial activity and completed the present invention.

The following are the detailed description of the processes of the present invention.

The process of the present invention is generally classified into two types as below:
(A) An antibiotic XK-62-2 is reacted with an acylating agent to introduce the acyl group α-hydroxy-δ-protected-amino-valeryl group or α-hydroxy-ε-protected-amino-caproyl group into the amino group at 1-position of the XK-62-2, whereby an intermediate compound is formed.
Thereafter, the amino-protecting group of the intermediate compound, i.e. the amino-protecting group for the amino group of the introduced acyl group, is removed to produce the desired compound.
(B) An antibiotic XK-62-2, whose amino groups bonded to the carbon atoms at 2'-position and/or 6'-position are protected, is reacted with an acylating agent to introduce the acyl group α-hydroxy-δ-protected-aminovaleryl group or α-hydroxy-ε-protected-amino-caproyl group into the amino group at 1-position of the XK-62-2, whereby an intermediate compound is formed.

Thereafter, all of the amino-protecting groups of the intermediate compound, i.e. the amino-protecting groups for the amino groups at 2'-and/or 6'- positions and that for the amino group of the introduced acyl group, are removed to produce the desired compound.

The process (B), of course, can provide a better yield of the desired product than the process (A).

The explanation of the process (A) is set forth below.

Process of acylating XK-62-2

One mole of XK-62-2 dissolved in an appropriate solvent is reacted with 0.4 to 2.5 moles, preferably, 0.7 to 1.5 moles of an acylating agent. The reaction temperature is −50° to 50° C, preferably, −20° to 20° C. The reaction is usually complete in 1 to 15 hours.

The reaction may proceed under the reaction conditions out of the above specified ranges, but the selectivity of the position to which the acyl group is introduced is greatly reduced or, otherwise, the acylating agent decomposes. Consequently, the production yield of the desired product is extremely decreased.

As the acylating agent for this reaction, α-hydroxy-δ-aminovaleric acid, α-hydroxy-ε-aminocaproic acid and functional derivatives at the carboxyl groups thereof having an acylating ability may be used. As the amino-protecting group, any readily eliminable protecting group usually used in peptide syntheses may be used. Such protecting groups and the corresponding protecting reagents which can introduce the protecting group are described in M. Bodanszky et al: Peptide Syntheses, pages 21–41 and 75–135, (1966) (John Wiley & Sons, Inc., U.S.A.) (hereinafter referred to as document A); A. Kapoor: Journal of Pharmaceutical Sciences, Vol. 59, pages 1–27 (1970) (hereinafter referred to as document B); and in M. Bodanszky et al: *Syntheses,* pages 453–463(1972) (hereinafter referred to as document C).

Examples of the preferred protecting groups and the corresponding reagents are shown below.

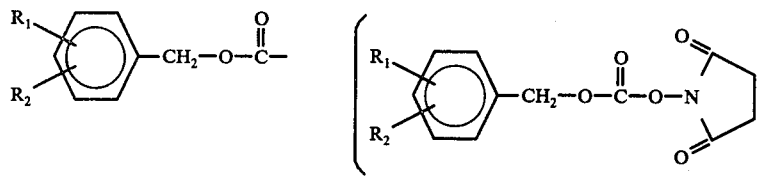

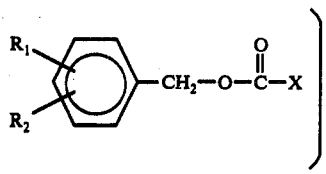

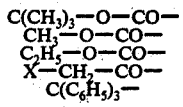 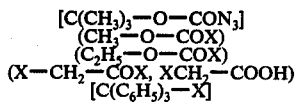

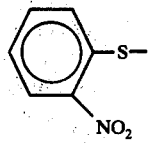 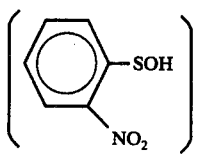

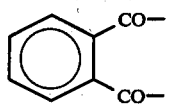 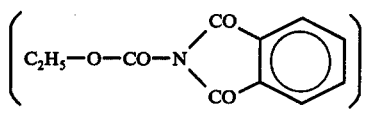

[$R_1$ and $R_2$ in the above formulae may be the same or different and are H, OH, $NO_2$, Cl, Br, I, alkyl groups having 1 to 5 carbon atoms or alkoxy groups having 1 to 5 carbon atoms, and X is Cl, Br or I]

As the functional derivative at the carboxyl group, various functional derivatives at carboxyl groups usually used in peptide synthesis such as acid halides, acid azide, mixed acid anhydride, and reactive ester, can be used; and the concrete examples are described in the afore-mentioned documents A, B and C.

As preferred functional derivatives, those having a structure in which the hydroxy group of the carboxyl group is substituted by one of the following groups are appropriate:

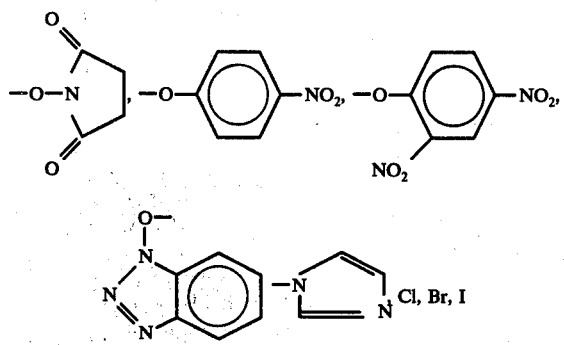

Particularly preferred acylating agents are those having a structure in which the OH group of the carboxyl group is substituted by

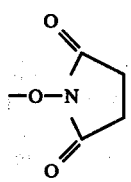

This compound is prepared by reacting α-hydroxy-δ-aminovaleric acid or α-hydroxy-ε-aminocaproic acid with N-hydroxysuccinimide in the presence of dehydrating and condensing agent such as dicyclohexylcarbodiimide.

The resulted reaction mixture containing the acylating agent can be used for the acylating reaction as it is, though the acylating agent may be isolated from the reaction mixture, then is used for the acylating reaction.

Other acylating agents may, of course, be used in the same manner as above.

The acylating reaction proceeds in the presence of dicyclohexylcarbodiimide, since XK-62-2 hardly reacts with α-hydroxy-δ-aminovaleric acid or α-hydroxy-ε-aminocaproic acid.

Certain cyanamides, etc. may be used in place of dicyclohexylcarbodiimide.

As the solvent for acylating reaction, is used at least one solvent selected from the group consisting of water, alcohols such as methanol, ethanol, 2-propanol, butanol, etc., amide class such as dimethylformamide, dimethylacetamide, etc., tetrahydrofuran, dioxane, ethylene glycol dimethyl ether, pyridine, and so on. A mixed solvent of ethanol and water (2 : 1 by volume) is especially preferred.

α-Hydroxy-δ-valeryl group or α-hydroxy-ε-caproyl group can be introduced to the amino group bonded to the carbon atom at the 1-position of XK-62-2 or its derivative whose amino groups at 2′-position and/or 6′-position are protected. This acylating method per se is described in the aforementioned documents A, B and C.

Eliminating process for amino-protecting group

Amino protecting group of the derivative of XK-62-2 obtained by the acylating reaction can be eliminated in the known manner of eliminating amino protecting group. For example, when the amino protecting groups are phthaloyl groups, elimination is accomplished with hydrazine; when the amino protecting groups are carbomethoxy groups or carboethoxy groups, elimination is accomplished with barium hydroxide; when the amino protecting groups are tertiary-butoxy carbonyl groups, elimination is accomplished with formic acid or trifluoroacetic acid; when the amino protecting groups are orthonitrophenylsulphenyl groups, elimination is accomplished with 3-nitropyridine-2-thione [reported by K. Undheim et al: *Journal of Chemical Society, Parkin Transaction I.* page 829 (1973)].

When the amino protecting groups are benzyloxycarbonyl groups, elimination is easily carried out by a hydrogenolysis at room temperature under atmospheric pressure with a small amount of acid such as hydrochloric acid, hydrobromic acid, hydriodic acid, acetic acid etc. in the presence of a metal catalyst such as palladium, platinum and so on, in at least one solvent selected from the group consisting of water, alcohols, tetrahydrofuran, dioxane, dimethylformamide, dimethylacetamide, ethylene glycol dimethyl ether, etc.

The desired product is isolated and purified from the thus obtained reaction mixture by a column chromatography using adsorbents such as ion exchange resins, silica gel, alumina and cellulose, or a thin layer chromatography using silica gel, alumina or cellulose.

The explanation of the process (B) is set forth below.

In this process, the amino groups of XK-62-2 are protected, in advance, at the 2'-position and/or the 6'-position, before XK-62-2 is subjected to the acylating reaction, since the reactivity of the amino group bonded to the carbon atom at 1-position of XK-62-2 is inferior to the reactivity of that at 2'-position or 6'-position of XK-62-2.

Process for protecting the amino groups bonded to the carbon atoms at the 2'- and/or 6'-positions of XK-62-2

The protecting groups are introduced to the amino groups bonded to the carbon atoms at the 2'-position and/or 6'-position of XK-62-2 by reacting XK-62-2 with an aminoprotecting reagent in an appropriate solvent under the same conditions as a usual manner to protect the amino groups.

It is preferable to react one mole of XK-62-2 with 1.0 to 4.5 moles, favourably, 1.5 to 2.6 moles of the protecting reagent at a temperature from −50° to 50° C preferably from −20° to 30° C.

The preferred examples of the protecting reagent and the solvent for this reaction are given and described in connection with the process of acylating XK-62-2 which is previously described.

This process per se is described in the aforementioned documents A, B and C.

Process for acylating the compound whose amino groups bonded to the carbon atoms at 2'-position and/or 6'-position of XK-62-2 are protected and process for eliminating the amino protecting groups from the resulted acylated product One mole of the starting material XK-62-2 whose amino groups bonded to the carbon atoms at 2'- and/or 6'-positions are, in advance, protected is reacted with 0.5 to 1.5 moles, preferably, 0.7 to 1.2 moles of an acylating agent.

The reaction may proceed, though the ratio of the reactants is out of the above range, but the selectivity of the position to which the acyl group is introduced is greatly reduced or, otherwise, the acylating agent decomposes. Consequently, the production yield of the desired product is extremely decreased.

As the acylating agent and the solvent for this reaction, the same materials as those used in the process for acylating XK-62-2 may also be used.

Elimination of the amino-protecting groups and isolation and purification of the desired product are carried out in a similar manner as in the case where XK-62-2 is used as the starting material.

As to chemical and physical analytical data such as nuclear magnetic resonance spectrum, infrared absorption spectrum, melting point, specific rotation, elementary analysis and the values of minimum inhibitory concentration against various kinds of bacteria, the product of (A) process and that of (B) process coincide each other.

1-N-(αhydroxy-δ-aminovaleryl)XK-62-2 and 1-N-(ε-hydroxy-ε-aminocaproyl)XK-62-2 of the present invention have an excellent antibacterial activity and are characterized by a strong antibacterial activity against *Escherichia coli* strains having R factors, which show a resistance to known aminoglycoside anitibiotics.

Table 1 illustrates minimum inhibitory concentration of 1-N-(α-hydroxy-δ-aminovaleryl)XK-62-2 and 1-N-(α-hydroxy-ε- aminocaproyl)XK-62-2 against various Gram-negative and Gram-positive bacteria determined by agar dilution method.

Table 1

| | Minimum Inhibitory Concentration, mcg/ml | | |
|---|---|---|---|
| Strains | XK-62-2 | 1-N-[L-(−)-α-hydroxy-δ-aminovaleryl]-XK-62-2 | 1-N-[L-(−)-α-hydroxy-ε-aminocaproyl]-XK-62-2 |
| *Pseudomonas aeruginosa* BMH No. 1 | 0.13 | 0.52 | 4.17 |
| *Staphylococcus aureus* ATCC 6538P | <0.004 | 0.008 | 0.033 |
| *Bacillus subtilis* No. 10707 | <0.004 | <0.004 | 0.008 |
| *Proteus vulgaris* ATCC 6897 | 0.016 | 0.065 | 0.26 |
| *Shigella sonnel* ATCC 9290 | 0.033 | 0.065 | 0.26 |
| *Salmonella typhosa* ATCC 9922 | 0.008 | 0.016 | 0.065 |
| *Klebsiella penumoniae* ATCC 10031 | <0.004 | 0.008 | 0.033 |
| *Escherichia coli* ATCC 26 | 0.016 | 0.033 | 0.13 |
| *Escherichia coli* KY 8327 | 1.04 | 0.065 | 0.013 |
| *Escherichia coli* KY 8348 | 1.04 | 0.033 | 0.065 |

In the above Table 1, *Escherichia coli* KY 8327 and KY 8348 respectively produce adenyltransferase and acetyltransferase intracellularly; the former enzyme inactivates kanamycins and gentamicins by adenylation, and the latter inactivates gentamicins by acetylation.

From the preceeding Table 1, it is apparent that 1-N-(α-hydroxy-δ-aminovaleryl)XK-62-2 and 1-N-(α-hydroxy-ε-aminocaproyl)XK-62-2 of the present invention have a very strong antibacterial activity, particularly, against *Escherichia coli* KY 8327 and *Escherichia coli* KY 8348 (both having a resistance to known aminoglycoside antibiotics, for instance, kanamycins and gentamicins).

These novel compounds of the present invention having such an eminent antibacterial activity as mentioned above are useful to clean and disinfect laboratory glassware and surgical instruments, and may also be used for pharmaceutical purpose and sanitation purpose in cleaning and sanitizing hospital rooms and areas.

Practice of certain specific embodiments of the present invention is illustrated by the following representative examples.

EXAMPLE 1

Production of
L-(−)-α-hydroxy-δ-carbobenzoxyaminovaleric acid

In this example, 1.33 g (10.0 mM) of L-(−)-α-hydroxy-δ-aminovaleric acid and 0.80 g (20.0 mM) of caustic soda are dissolved in 13.0 ml of water. To the solution is added dropwise 2.04 g (12.0 mM) of carbobenzoxy chloride with stirring, at a temperature of 0° to 5° C. The addition is complete in one hour. The mixture is subjected to reaction at the same temperature for further 3 hours.

To the resulting reaction mixture is added 20 ml of ether to remove unreacted carbobenzoxychloride. The resulting aqueous solution is adjusted to pH 2.0 with concentrated hydrochloric acid. The aqueous solution is extracted three times each with 15 ml of ether. The ether extracts are combined and washed with an aqueous saturated sodium chloride solution and then dried with anhydrous sodium sulfate. Then, the ether is removed off. The resulting crystals are recrystallized from a mixed solvent of ethyl acetate and normalhexane, to obtain 2.20 g of pure product.

Yield: 82.5%
Melting point: 113.0° − 113.5° C
Specific rotation: $[\alpha]_D^{27} + 2.40°$ (c=2.0 methanol)
Infrared absorption spectrum (KBr, cm$^{-1}$)
  3460, 3350, 2930, 1726, 1688, 1531, 1451, 1279, 1140, 1116, 1031, 728, 690.
Nuclear magnetic resonance spectrum (in methanol-$d_4$) δ (in p.p.m. from TMS)
  1.73(4H, m), 3.20(2H, m), 4.20(1H, broad s), 5.14(2H, s), 7.43(5H, s)
Elementary analysis: Calculated for $C_{13}H_{17}NO_5$: C, 58.42; H, 6.41; N, 5.24(%); Found: C, 58.45; H, 6.48; N, 5.45(%)

EXAMPLE 2

Production of N-hydroxysuccinimide ester of
L-(−)-α-hydroxy-δ-carbobenzoxyaminovaleric acid In this example, 0.53 g (2.0 mM) of L-(−)-α-hydroxy-δ-carbobenzoxyaminovaleric acid and 0.23 g (2.0 mM) of N-hydroxysuccinimide are dissolved in 20 ml of ethyl acetate. To the solution is added 0.41 g (2.0 mM) of N,N′-dicyclohexylcarbodiimide at a temperature of 0° to 5° C. The mixture is allowed to react at the same temperature overnight. The resulting precipitate of N,N′-dicyclohexylurea is removed by filtration and the resulting filtrate is evaporated under reduced pressure. As the result, 0.71 g of the desired product is obtained as a colorless transparent viscous oily matter.

Yield: 96.5%
Infrared absorption spectrum (neat cm$^{-1}$)
  νc=0 1810, 1785, 1725

EXAMPLE 3

Production of
1-N-[L-(−)-α-hydroxy-δ-carbobenzoxyaminovaleryl]XK-62-2

In this example, 0.46 g (1.0 mM) of XK-62-2 is dissolved in 25 ml of aqueous 50% dimethylformamide. To the solution is added dropwise 0.44 g (1.2 mM) of N-hydroxysuccinimide ester of L-(−)-α-hydroxy-δ-carbobenzoxyaminovaleric acid in 10 ml of dimethylformamide with stirring at a temperature of −5° to 0° C. The addition is complete in one hour and the mixture is allowed to react overnight. The reaction mixture is concentrated under reduced pressure, to obtain a yellowish residue containing the desired product. The thus obtained residue is ready for use as the starting material for the subsequent reaction without purification.

EXAMPLE 4

Production of
1-N-[L-(−)-α-hydroxy-δ-aminovaleryl]XK-62-2

In this example, the residue obtained in Example 3 is dissolved in 20 ml of aqueous 50% methanol. To the solution is added 0.3 ml of acetic acid and the mixture is subjected to hydrogenolysis in the presence of 40 mg of 5% active carbonpalladium catalyst at room temperature and atmospheric pressure for 6 hours. By silica gel thin layer chromatography (developer is isopropanol: concentrated aqueous ammonia: chloroform=2 : 1 : 1) in addition to the desired compound (Rf value: 0.33), there are found its positional isomers and XK-62-2 in a small amount. The catalyst is removed by filtration and the filtrate is concentrated under reduced pressure. The resulting residue is then dissolved in 5 ml of water and the solution is charged into a column (diameter: 1.5 cm) of ion exchange resin Amberlite CG-50 (ammonium form 30 ml). The column is washed with 150 ml of water. Then 0.2N aqueous ammonia is passed through the column, to recover XK-62-2 (79 mg). A further elution is carried out with 0.4N aqueous ammonia checking the components of the eluate by a thin layer chromatography. The eluate is taken in portions. The fractions containing only the desired product are combined and concentrated under reduced pressure, to obtain 67 mg of a colorless, amorphous solid.

Yield: 10.2%
Melting point: 144° − 147° C
Specific rotation: $[\alpha]_D^{18} + 55.0°$ (c=0.100 water)
Infrared absorption spectrum (KBr, cm$^{-1}$)
  3400, 2950, 1650, 1565, 1481, 1386, 1340, 1112, 1057, 1026, 818.
Nuclear magnetic resonance spectrum (in $D_2O$) δ (in p.p.m. from DSS)
  1.19(3H, s), 2.50(3H, s), 2.67(3H, s), 5.1 − 5.5(2H, m)
Elementary analysis: Calculated for $C_{25}H_{50}N_6O_9 \cdot H_2CO_3 \cdot H_2O$: C, 47.42; H, 8.21; N, 12.77(%); Found: C, 47.14; H, 8.16; N, 12.36(%)

EXAMPLE 5

Production of monosulfate of
1-N-[L-(−)-α-hydroxy-δ-aminovaleryl]XK-62-2

In this example, 0.66 g (1.0 mM) of 1-N-[L-(−)-α-hydroxy-δ-aminovaleryl]XK-62-2 is dissolved in 5 ml of water. To the solution is added a solution of 0.098 g (1.0 mM) of sulfuric acid in 1 ml of water under cooling. After 30 minutes, cold methanol is added to the mixture until precipitation is complete. The precipitated white solid is recovered by filtration to obtain the desired monosulfate.

EXAMPLE 6

Production of
L-(−)-α-hydroxy-ε-carbobenzoxyaminocaproic acid

In this example, 1.47 g (10.0 mM) of L-(−)-α-hydroxy-ε-aminocaproic acid and 0.80 g (20.0 mM) of caustic soda are dissolved in 15 ml of water. To the solution is added dropwise 2.04 g (12.0 mM) of carbobenzoxy chloride with stirring at a temperature of 0° to 5° C. The addition is complete in one hour. The mixture is subjected to reaction for further 3 hours at the same temperature. To the solution is added 20 ml of ether to remove unreacted carbobenzoxychloride. The resulting aqueous solution is adjusted to pH 2.0 with concentrated hydrochloric acid. The aqueous solution is extracted three times with each 15 ml of ether. The ether extracts are combined and washed with an aqueous saturated sodium chloride solution, and then the ether extracts are dried with anhydrous sodium sulfate. The ether is removed off. The resulting crystals are recrystallized from a mixed solvent of ethyl acetate and normal-hexane, to obtain 2.20 g of pure desired product.

Yield: 78.2%
Melting point: 84.0° – 84.5° C
Specific rotation: $[\alpha]_D^{27} + 0.64°$ (c=2.0 methanol)
Infrared absorption spectrum (KBr, cm$^{-1}$)
  3460, 3320, 2940, 1739, 1680, 1532, 1451, 1274, 1139, 1122, 1098, 900, 746, 693.
Nuclear magnetic resonance spectrum (in CDCl$_3$) δ (in p.p.m. from TMS)
  1.55(6H, m), 3.23(2H, broad s), 4.30(1H, broad s), 5.19(2H, s), 5.96(3H, broad s), 7.45(5H, s)
Elementary analysis: Calculated for $C_{14}H_{19}NO_5$: C, 59.78; H, 6.81; N, 4.98(%); Found: C, 59.73; H, 6.83; N, 4.96(%)

EXAMPLE 7

Production of N-hydroxysuccinimide ester of L-(−)-α-hydroxy-ε-carbobenzoxyaminocaproic acid In this example, 0.56 g (2.0 mM) of L-(−)-α-hydroxy-ε-carbobenzoxyaminocaproic acid and 0.23 g (2.0 mM) of N-hydroxysuccinimide are dissolved in 20 ml of ethyl acetate. To the solution is added 0.41 g (2.0 mM) of N,N′-dicyclohexylcarbodiimide at a temperature of 0° to 5° C. The mixture is allowed to react at the same temperature overnight. The resulting precipitate of N,N′-dicyclohexylurea is removed by filtration and the resulting filtrate is evaporated under reduced pressure. As the result, 0.72 g of the desired product is obtained as a colorless transparent viscous oily matter.

Yield: 95.0%
Infrared absorption spectrum (neat cm$^{-1}$)
  νc=0 1812, 1787, 1724

EXAMPLE 8

Production of 1-N-[L-(−)-α-hydroxy-ε-carbobenzoxyaminocaproyl]XK-62-2

In this example, equal amount moles of N-hydroxysuccinimide ester of L-(−)-α-hydroxy-ε-carbobenzoxyaminocaproic acid is used in place of N-hydroxysuccinimide ester of L-(−)-α-hydroxy-δ-carbobenzoxyaminovaleric acid in the procedures in Example 3, to obtain the above-mentioned desired product.

EXAMPLE 9

Production of 1-N-[L-(−)-α-hydroxy-ε-aminocaproyl]XK-62-2

In this example, equal amount moles (1.2 mM) of 1-N-[L-(−)-α-hydroxy-ε-carbobenzoxyaminocaproyl]XK-62-2 obtained in Example 8 is used in place of 1-N-[L-(−)-α-hydroxy-δ-carbobenzoxyaminovaleryl]XK-62-2 obtained as a residue in Example 3 for the subsequent reaction, in the procedures in Example 4, to obtain 58 mg of the above-mentioned desired product.

Yield: 8.3%
Melting point: 140° – 145° C
Specific rotation: $[\alpha]_D^{18} + 82.2°$ (c=0.110 water)
Infrared absorption spectrum: (KBr, cm$^{-1}$)
  3400, 2940, 1640, 1567, 1480, 1385, 1340, 1112, 1055, 1020, 813.
Nuclear magnetic resonance spectrum (in D$_2$O) δ (in p.p.m. from DSS)
  1.23(3H, s), 2.63(3H, s), 2.73(3H, s), 5.1 – 5.5(2H, m)
Elementary analysis: Calculated for $C_{25}H_{50}N_6O_9 \cdot 2H_2CO_3$: C, 46.15; H, 7.74; N, 11.96(%); Found: C, 46.90; H, 8.04; N, 11.51(%)

EXAMPLE 10

Production of monosulfate of 1-N-[L-(−)-α-hydroxy-ε-aminocaproyl]XK-62-2

In this example, equal amount moles of 1-N-[L-(−)-α-hydroxy-ε-aminocaproyl]XK-62-2 is used in place of 1-N-[L-(−)-α-hydroxy-δ-aminovaleryl]XK-62-2 in the procedures in Example 5, to obtain the desired monosulfate.

EXAMPLE 11

Production of 2′-N,6′-N-dicarbobenzoxy XK-62-2

In this example, 4.00 g (8.65 mM) of XK-62-2 is dissolved in 92 ml of aqueous 50% dimethylformamide. To the solution is added dropwise a solution of 3.23 g (12.9 mM) of N-benzyloxycarbonyloxy-succinimide in 70 ml of dimethylformamide with stirring at a temperature of 0° to 5° C. The addition is complete in 3 hours. The mixture is allowed to stand at 0° to 5° C overnight. By silica gel thin layer chromatography (developer is isopropanol: concentrated aqueous ammonia: chloroform=4 : 1 : 1, color reagent is ninhydrin) the presence of unreacted XK-62-2 in addition to 6′-N-carbobenzoxy-XK-62-2 (Rf: 0.71), 2′-N-carbobenzoxy XK-62-2 (Rf: 0.62) and 2′-N,6′-N-dicarbobenzoxy XK-62-2 (Rf: 0.88) is confirmed. The reaction mixture is concentrated under reduced pressure. To the resulting residue are added 70 ml of water and 50 ml of ethyl acetate. The mixture is stirred vigorously, then allowed to stand to separate into two layers: they are a water layer and an ethylacetate layer. The water layer is extracted twice with each 30 ml of ethylacetate. Both the ethylacetate layer and the ethylacetate extracts are combined, dried with anhydrous sodium sulfate and evaporated to dryness. As a result, 2.24 g of 2′-N,6′-N-dicarbobenzoxy XK-62-2 is obtained as a light yellowish amorphous solid. Yield: 35.1%.

The thus obtained product may be ready for use as a starting material for the subsequent reaction. However, if desired, the product may be further purified by silica gel column chromatography (developer is isopropanol: concentrated aqueous ammonia: chloroform=4 : 1 : 1).

Melting point: 93° – 95° C
Specific rotation: $[\alpha]_D^{18} + 81.6°$ (c=0.12 methanol)
Infrared absorption spectrum (KBr, cm$^{-1}$)
  3800 – 3000, 2950, 1700, 1540, 1456, 1403, 1310, 1250, 1160, 1050, 1010, 960, 738, 700, 605.
Nuclear magnetic resonance spectrum (in methanol −d$_4$) δ (in p.p.m. from TMS)
  1.13(3H, s), 2.62(3H, s), 3.01(3H, s), 5.30 – 4.90(6H, broad, s), 7.43(5H, s), 7.47(5H, s)

Elementary analysis: Calculated for $C_{36}H_{55}N_5O_{12}\cdot\frac{1}{2}H_2O$: C, 58.10; H, 7.29; N, 9.46(%); Found: C, 58.02; H, 7.51; N, 9.70(%)

EXAMPLE 12

Production of 6'-N-carbobenzoxy XK-62-2

In this example, the water layer obtained after extraction with ethyl acetate in Example 11 is concentrated to about 15 ml under reduced pressure. The resulting concentrate is charged into a column (diameter: 2.5 cm) packed with ion exchange resin Amberlite CG-50 (ammonium form, 200 ml). The column is washed with 200 ml of water. Elution is carried out with 0.1N aqueous ammonia while taking the eluate in 10 ml portions. 6'-N-carbobenzoxy XK-62-2 is eluted out in fraction Nos. 48 – 65. These fractions are combined and concentrated to dryness under reduced pressure. As the result, 1.23 g of a colorless amorphous solid is obtained.

Yield: 23.1%

The thus obtained product may be ready for use as a starting material for the subsequent reaction. However, if desired, the product may be further purified by repeating the above-mentioned column chromatography.

Melting point: 108° – 110° C

Specific rotation: $[\alpha]_D^{18} + 127.8°$ (c=0.094 methanol)

Infrared absorption spectrum (KBr, cm$^{-1}$)
3700 – 3000, 2930, 1690, 1596, 1480, 1452, 1402, 1250, 1143, 1096, 1050, 1020, 830, 768, 750, 697, 595, 550.

Nuclear magnetic resonance spectrum (in methanol $-d_4$) $\delta$ (in p.p.m. from TMS)
1.16(3H, s), 2.61(3H, s), 3.01(3H, s), 5.30 – 4.90(4H, m), 7.47(5H, s)

Elementary analysis: Calculated for $C_{28}H_{47}N_5O_9\cdot H_2O$: C, 54.77; H, 7.84; N, 11.13(%); Found: C, 54.91; H, 7.93; N, 10.90(%)

EXAMPLE 13

Production of 2'-N-carbobenzoxy XK-62-2

In this example, following the elution of 6'-N-carbobenzoxy XK-62-2 in Example 12, 2'-N-carbobenzoxy XK-62-2 is eluted out in fractions Nos. 78 – 97. These fractions are combined and concentrated to dryness under reduced pressure. As the result, 1.43 g of colorless amorphous solid is obtained. The thus obtained product may be ready for use as a starting material for the subsequent reaction. However, if desired, the product may be further purified by repeating the above-mentioned column chromatography.

Yield: 26.7%

Melting point: 107° – 110° C

Specific rotation: $[\alpha]_D^{25} + 87.8°$ (c=0.10 water)

Infrared absorption spectrum (KBr, cm$^{-1}$)
3700 – 3100, 2930, 1702, 1530, 1451, 1310, 1255, 1141, 1053, 1021, 960, 735, 697, 604.

Nuclear magnetic resonance spectrum (in methanol $-d_4$) $\delta$ (in p.p.m. from TMS)
1.13(3H, s), 2.42(3H, s), 2.60(3H, s), 5.13(4H, broad, s)

Elementary analysis: Calculated for $C_{28}H_{47}N_5O_9\cdot 2H_2O$: C, 53.08; H, 8.06; N, 11.06(%); Found: C, 53.31; H, 8.16; N, 10.93(%)

EXAMPLE 14

Production of 1-N-[L-(−)-α-hydroxy-δ-carbobenzoxyaminovaleryl]-2'-N,6'-N-dicarbobenzoxy XK-62-2

In this example, 0.76 g (1.0 mM) of 2'-N,6'-N-dicarbobenzoxy XK-62-2 obtained in Example 11 is dissolved in 20 ml of an aqueous 50% dimethylformamide. To the solution while maintaining at 0° – 5° C is added dropwise, with stirring, 0.44 g (1.2 mM) of N-hydroxysuccinimide ester of L-(−)-α-hydroxy-δ-carbobenzoxyaminovaleric acid dissolved in 15 ml of dimethylformamide.

The addition is complete in one hour. The mixture is allowed to react overnight. This reaction mixture is concentrated under reduced pressure to obtain a yellowish residue containing the above-mentioned compound. The residue is used for the subsequent reaction without purification.

EXAMPLE 15

Production of 1-N-[L-(−)-α-hydroxy-δ-carbobenzoxyaminovaleryl]-6'-N-carbobenzoxy XK-62-2

In this example, equal amount moles of 6'-N-carbobenzoxy XK-62-2 obtained in Example 12 is used in place of 2'-N,6'-N-dicarbobenzoxy XK-62-2 in the procedures in Example 14, to obtain the above-mentioned desired product.

EXAMPLE 16

Production of 1-N-[L-(−)-α-hydroxy-δ-carbobenzoxyaminovaleryl]-2'-N-carbobenzoxy XK-62-2

In this example, equal amount moles of 2'-N-carbobenzoxy XK-62-2 obtained in Example 13 is used in place of 2'-N,6'-N-dicarbobenzoxy XK-62-2 in the procedures in Example 14, to obtain the above-mentioned desired product.

EXAMPLE 17

Production of 1-N-[L-(−)-α-hydroxy-δ-aminovaleryl]XK-62-2

In this example, the residue obtained in Example 14 mainly containing 1-N-[L-(−)-α-hydroxy-δ-carbobenzoxyaminovaleryl]-2'-N,6'-N-dicarbobenzoxy XK-62-2 is dissolved in 20 ml of aqueous 20% methanol. To the solution is added 1.0 ml of acetic acid and the mixture is subjected to hydrogenolysis in the presence of 120 mg of 5% active carbonpalladium catalyst at room temperature under atmospheric pressure for 6 hours. By silica gel thin layer chromatography (the conditions are same as in Example 4), the presence of 1-N-[L-(−)-α-hydroxy-δ-aminovaleryl]XK-62-2 as a main component, a small amount of XK-62-2 (due to unreacted 2'-N,6'-N-dicarbobenzoxy XK-62-2 in Example 14), and the substituted positional isomers of 1-N-[L-(−)-α-hydroxy-δ-aminovaleryl]XK-62-2 is confirmed. The catalyst is removed by filtration and the filtrate is concentrated under reduced pressure. The residue is then dissolved in 10 ml of water and the solution is charged into a column (diameter: 1.5 cm) packed with ion exchange resin, Amberlite CG-50 (ammonium form 50 ml). The column is washed with 200 ml of water.

Then 0.2N aqueous ammonia is passed through the column and 78 mg of XK-62-2 is recovered. A further elution is carried out with 0.4N aqueous ammonia, while checking the components of the eluate by thin layer chromatography. The eluate is taken in portions. The fractions containing only 1-N-[L-(—)-α-hydroxy-δ-aminovaleryl]XK-62-2 are combined and concentrated under reduced pressure to dryness. The obtained product is 0.36 g of colorless amorphous solid.

Yield: 54.6% (from 2'-N,6'-N-dicarbobenzoxy XK-62-2)

EXAMPLE 18

Production of
1-N-[L-(—)-α-hydroxy-δ-aminovaleryl]XK-62-2

In this example, the residue obtained in Example 15 mainly containing 1-N-[L-(—)-α-hydroxy-δ-carbobenzoxyaminovaleryl]-6'-N-carbobenzoxy XK-62-2 is treated in the same manner as in Example 17, to obtain the above-mentioned desired product.

EXAMPLE 19

Production of
1-N-[L-(—)-α-hydroxy-δ-aminovaleryl]XK-62-2

In this example, the residue obtained in Example 16 containing mainly 1-N-[L-(—)-α-hydroxy-δ-carbobenzoxyaminovaleryl]-2'-N-carbobenzoxy XK-62-2 is treated in the same manner as in Example 17, to obtain the above-mentioned desired product.

EXAMPLE 20

Production of
1-N-[L-(—)-α-hydroxy-ε-carbobenzoxyaminocaproyl]-2'-N,6'-N-dicarbobenzoxy XK-62-2

In this example, equal amount moles of N-hydroxysuccinimide ester of L-(—)-α-hydroxy-ε-carbobenzoxyaminocaproic acid is used in place of N-hydroxysuccinimide ester of L-(—)-α-hydroxy-δ-carbobenzoxyaminovaleric acid in the procedures in Example 14, to obtain the above-mentioned desired product.

EXAMPLE 21

Production of
1-N-[L-(—)-α-hydroxy-ε-carbobenzoxyaminocaproyl]-6'-N-carbobenzoxy XK-62-2

In this example, equal amount moles of N-hydroxysuccinimide ester of L-(—)-α-hydroxy-ε-carbobenzoxyaminocaproic acid is used in place of N-hydroxysuccinimide ester of L-(—)-α-hydroxy-δ-carbobenzoxyaminovaleric acid in the procedures in Example 15, to obtain the above-mentioned desired product.

EXAMPLE 22

Production of
1-N-[L-(—)-α-hydroxy-ε-carbobenzoxyaminocaproyl]-2'-N-carbobenzoxy XK-62-2

In this example, equal amount moles of N-hydroxysuccinimide ester of L-(—)-α-hydroxy-ε-carbobenzoxyaminocaproic acid is used in place of N-hydroxysuccinimide ester of L-(—)-α-hydroxy-δ-carbobenzoxyaminovaleric acid in the procedures in Example 16, to obtain the above-mentioned desired product.

EXAMPLE 23

Production of
1-N-[L-(—)-α-hydroxy-ε-aminocaproyl]XK-62-2

In this example, the residues obtained in Examples 20, 21 and 22 mainly containing 1-N-[L-(—)-α-hydroxy-ε-carbobenzoxyaminocaproyl]-2'-N,6'-N-dicarbobenzoxy XK-62-2, 1-N-[L-(—)-α-hydroxy-ε-carbobenzoxyaminocaproyl]-6'-N-carbobenzoxy XK-62-2 and 1-N-[L-(—)-α-hydroxy-ε-carbobenzoxyaminocaproyl]-2'-N-carbobenzoxy XK-62-2 respectively are treated separately in the same manner as in Example 17 to obtain the above-mentioned desired product.

What is claimed is:

1. A composition of matter having an antibacterial activity represented by the formula:

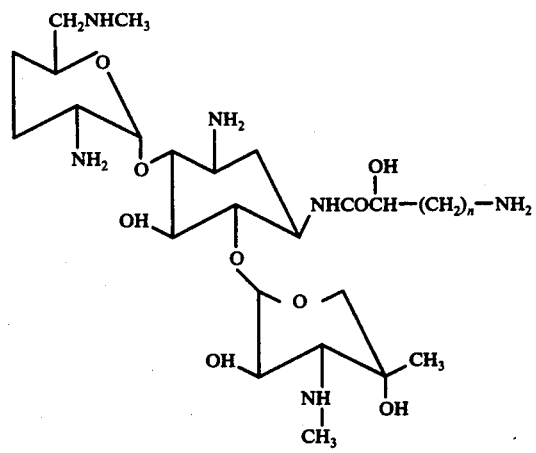

wherein $n$ is the integer 3 or 4.

2. The composition of matter of claim 1 wherein $n$ is the integer 3, said composition of matter being 1-N-(α-hydroxy-δ-aminovaleryl) XK-62-2.

3. A nontoxic pharmaceutically acceptable acid addition salt of the composition of matter of claim 2, said acid being selected from the group consisting of hydrochloric acid, hydrobromic acid, hydriodic acid, sulfuric acid, phosphoric acid, carbonic acid, acetic acid, fumaric acid, malic acid, citric acid, mandelic acid, tartaric acid, succinic acid and ascorbic acid.

4. The composition of matter of claim 1 wherein $n$ is the integer 4, said composition of matter being 1-N-(α-hydroxy-ε-aminocaproyl) XK-62-2.

5. A nontoxic pharmaceutically acceptable acid addition salt of the composition of matter of claim 4, said acid being selected from the group consisting of hydrochloric acid, hydrobromic acid, hydriodic acid, sulfuric acid, phosphoric acid, carbonic acid, acetic acid, fumaric acid, malic acid, citric acid, mandelic acid, tartaric acid, succinic acid and ascorbic acid.

* * * * *